United States Patent
Barak

[19]

[11] Patent Number: 5,951,510
[45] Date of Patent: Sep. 14, 1999

[54] PUMP SYSTEM WITH ERROR DETECTION FOR CLINICAL NUTRITION

[75] Inventor: Swi Barak, Caesarea, Israel

[73] Assignee: Nestec S.A., Vevey, Sweden

[21] Appl. No.: 09/031,032

[22] Filed: Feb. 26, 1998

[30] Foreign Application Priority Data

Apr. 11, 1997 [IL] Israel ......................................... 120651

[51] Int. Cl.$^6$ .................................................. A61M 31/00
[52] U.S. Cl. ............................................. 604/67; 604/151
[58] Field of Search ............................ 604/151, 67, 141, 604/153, 65, 131; 128/DIG. 13

[56] References Cited

U.S. PATENT DOCUMENTS

| | | | |
|---|---|---|---|
| 3,901,231 | 8/1975 | Olson | 128/DIG. 13 |
| 4,278,085 | 7/1981 | Shim | 604/153 |
| 4,530,696 | 7/1985 | Bisera et al. | |
| 4,846,792 | 7/1989 | Bobo, Jr. et al. | |
| 5,312,334 | 5/1994 | Hara et al. | 604/65 |
| 5,356,378 | 10/1994 | Doan | 128/DIG. 13 |
| 5,423,743 | 6/1995 | Butterfield | |
| 5,472,420 | 12/1995 | Campbell | |
| 5,621,392 | 4/1997 | Paolini et al. | 128/DIG. 13 |
| 5,695,473 | 12/1997 | Olsen | 128/DIG. 13 |

FOREIGN PATENT DOCUMENTS

| | | | |
|---|---|---|---|
| 0279028 | 8/1988 | European Pat. Off. | 604/131 |
| 0 335 385 | 10/1989 | European Pat. Off. | |
| 529829 | 3/1993 | European Pat. Off. | 604/131 |
| 638328 | 2/1995 | European Pat. Off. | 604/131 |
| WO 87/05225 | 9/1987 | WIPO | |
| WO 95/16480 | 6/1995 | WIPO | |

*Primary Examiner*—Jeffrey A. Smith
*Assistant Examiner*—Eduardo C. Robert
*Attorney, Agent, or Firm*—Hill & Simpson

[57] ABSTRACT

A pump for delivering a liquid from a container to a patient through a flow set. The pump includes a sensing means and a controller. The sensing means senses a parameter indicative of the pressure in the flow set. The controller has a computing and memory means for determining deviation of the parameter from a standard. Deviation is indicative of an error in the flow set. This enables supervising staff to be alerted. These errors may be incorrect assembly of the system or one of its components, inclusion in the system of an incorrect valve, impairment in the integrity of the flow set, and the existence of air bubbles in the system.

14 Claims, 3 Drawing Sheets

PUMP SYSTEM WITH ERROR DETECTION FOR CLINICAL NUTRITION

FIELD OF THE INVENTION

This invention relates generally to a pump system for administering liquids to a patient; for example medicinal or nutritional solutions. The liquids may be administered enterally or parenterally. The invention also relates to a pump for use in the system and to methods of administering liquids to a patient.

BACKGROUND OF THE INVENTION

Systems for administering liquids to a patient are widely used in clinical settings. All of these systems comprise a container for the liquid and a flow set for delivering the liquid to the patient. In general, the liquid is either allowed to drain through the flow set to the patient under the action of gravity or is pumped through the flow set. Systems Using pressure sleeves on the container are also used. Systems using a pump are referred to in this specification as "pump systems".

The rate of flow of the liquid through the system is usually set to a desired rate depending on the needs of the patient. In pump systems this may be achieved by controlling the pump rate. However, particularly when intended for intravenous administration of liquids, it is important to ensure that there will be no back flow of liquid in the tubing, that is away from the patient. To prevent this, a one-way valve is typically installed in the flow set. Further, because the container is typically mounted on a stand it is necessary to ensure that free-flow of liquid due to the liquid head will not occur when the pump is at rest. For this purpose, the valve, in addition to being a one-way valve, also needs to prevent free flow. Therefore the valve has a certain threshold pressure which is required to open it to allow flow of liquid. The threshold pressure is also known as the "cracking point". Pump systems containing such a valve are described in PCT Application WO 95/16480 and U.S. Pat. No. 5,472,420. However, incorrect valves are occasionally connected in the flow sets with serious consequences.

It is also important to ensure that the flow set, which is typically provided as an integral disposable set, is correctly connected to the pump to avoid pumping of liquid in a reverse direction, away from the patient. This is often left to the supervising staff and errors do occur. Also, flow sets occasionally fail and this is often not noticed until too late.

It is therefore an object of the invention to provide a pump system which automatically detects errors which may impair the proper functioning of the system.

SUMMARY OF THE INVENTION

Accordingly, in one aspect, this invention provides a pump for delivering a liquid from a container to a patient through a flow set, the pump including:
  a sensing means for sensing a parameter indicative of the pressure in the flow set; and
  a controller having a computing and memory means for determining deviation of the parameter from a standard, the deviation being indicative of an error in the flow set.

It has been surprisingly discovered that, by measuring the pressure in the flow set and comparing it to a standard, errors in the system may be detected. This enables supervising staff to be alerted. These errors may, for example, be incorrect assembly of the system or one of its components, inclusion in the system of an incorrect valve, impairment in the integrity of the flow set, and the existence of air bubbles in the system.

In another aspect, this invention provides a pump system for administering a liquid from a container to a patient, the system comprising:
  flow set comprising a tubing set connectable at one end to the container for delivery of liquid to the patient, and a one-way valve system coupled to the tubing set which permits liquid flow to the patient when a pressure differential over the valve exceeds a threshold pressure, and which prevents back flow;
  a pump as define d above coupled to the tubing set.

Preferably, the controller causes the pump, during operation of the pump, to either into a test phase at selected intervals, the test phase comprising a first test sequence in which the pump propels a first amount of liquid in a first direction through the flow set, and a second test sequence in which the pump propels a second amount of liquid through the flow set in a second direction, opposite the first. The sensing means senses the parameter during the first test sequence and the second test sequence.

The valve system preferably comprises a valve having a liquid flow path sealed by a resilient membrane, the membrane being deformable in a desired flow direction at or above a threshold pressure for opening perforations in the membrane to permit flow. Further, the valve preferably has a support preventing the membrane from deforming sufficiently in an opposite flow direction for preventing back flow.

In further aspect, this invention provides a method for administering a liquid from a container to patient using a pump system, the method comprising:
  pumping liquid through a flow set from the container to the patient through a one-way valve system which permits flow to the patient when the pressure differential over the valve system exceeds a threshold pressure, and which prevents back flow; and
  intermittently entering a test phase comprising
    pumping a first test amount of liquid in a first direction and then pumping a second test amount of liquid in an opposite direction,
    sampling a parameter indicative of pressure within the flow set during pumping of the first test amount of liquid and during pumping of second test amount of liquid, and
    comparing the sampled parameters to a standard and, upon determining a difference of selected magnitude between the sampled parameters and the standard, indicating the existence of an error in the pump system.

The error which is diagnosed by the system, may, for example be:
  the impairment of liquid flow through the flow set as a result of an occlusion, a rupture or a hole in the tubing, or disengagement of components of the flow set, etc.;
  incorrect engagement of the pump with the flow set, for example engagement in a reverse direction;
  the use of incompatible components in the flow set, for example the use of an improper valve having improper flow specifications; or
  changes in the flow parameters of the valve during operation, for example the existence of gas bubbles or gas pockets in the tubing; etc.

The present invention also provides a flow set for use in the system of the invention.

BRIEF DESCRIPTION OF THE DRAWINGS

Embodiments of the invention are now described, by way of example only, with reference to the drawings in which.

DETAILED DESCRIPTION OF PREFERRED EMBODIMENTS

Figure 1:
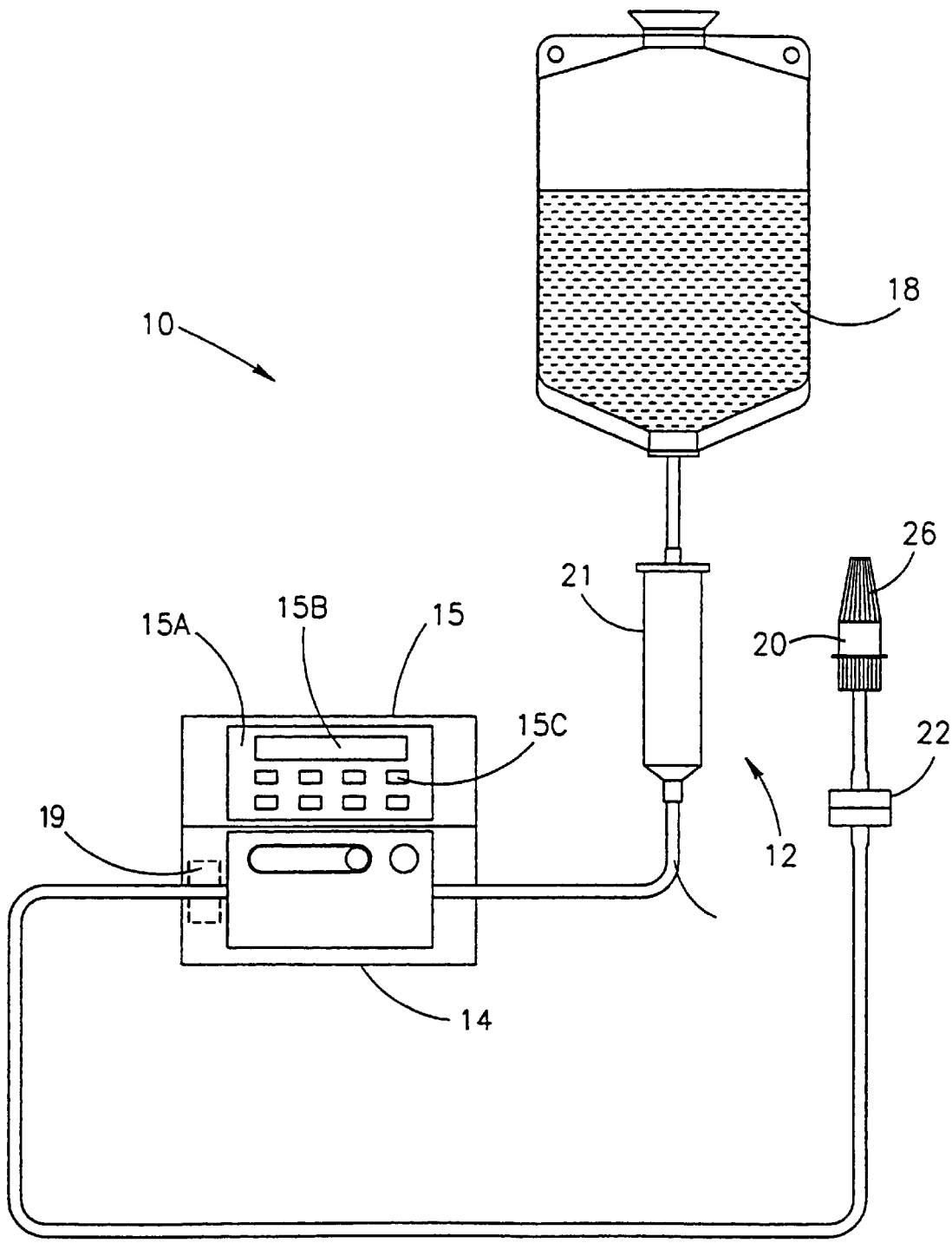
FIG. 1 is a schematic illustration of a pump system.

A pump system 10 is illustrated in FIG. 1. The pump system 10 comprises a pump 14 with a control unit 15, and a flow set 12. The pump 14 is preferably a peristaltic pump but any type of pump which is able to liquid at controlled flow rates suitable for clinical applications may be used. The control unit 15 typically comprises a control panel 15a which has a display 15b and a key pad 15c. The key pad 15c may be used for manual control of the pump, data entry, and the like. The control unit 15 also includes a microprocessor (not shown) for controlling and activating the pump and for data storage. A memory (not shown) may be associated with., or be incorporated in, the microprocessor. If desired, the control unit 15 may also include an audio, visual or dual alarm signaling means.

The flow set 12 is made up of a tubing set 16 which is connected to a liquid container 18 at one end and a connector 20 at the other end. A drip chamber 21 and a one-way valve 22 are coupled to the tubing set 16 between its ends. In this embodiment, the drip chamber 21 is positioned beneath the liquid container 18, upstream from the pump 14. The one-way valve 22 is positioned downstream from the pump 14. As is conventional, the connector 20 may be connected to a catheter, an enteral feeding tube, etc. When not in use, the free end of the connector 20 is covered by a cover 26.

The pump 14 is coupled to the tubing set 16 and is able to pump liquid in either direction. Therefore, from the container 18 to the connector 20 (the forward direction), and towards the container 18 (the reverse direction).

The pump 14 also includes a sensing means 19 for sensing a parameter indicative of the pressure in the flow set 12. The sensing means 19 is conveniently a tube diameter gauge which measures the diameter of the tubing set 16. Then, using the known resiliency of the tubing set 16, the pressure in the tubing, set 16 may be determined by the microprocessor. The tube diameter may for example, be a strain gauge, an optical sensor, and the like. Alternatively, other known means of determining pressure in the tubing set 16 may be used. For example, conventional pressure gauges may be connected into the tubing set 16. The pressure parameter is preferably repeatedly sampled at short time intervals so that a curve of pressure change with time may be developed.

The-one-way valve 22, shown in cross-section in FIG. 2, has a housing 30 formed of a first housing member 32 and a second housing member 34. The first housing member 32 has a recess in it into which the second housing member 34 is accommodated in a sealed manner. The second housing member 34 also has a recess in it so that a chamber 35 is defined between the first and second housing members 32, 34.

The first housing member 32 has an inlet tube 36 which is connected to the chamber 35 by means of an entry port 37. An annular rim 38 projects into the chamber 35 from the floor of the recess of the first housing member 32, about entry port 37. The second housing member 34 has an outlet tube 39 which is connected to the chamber 35 by means of an exit port 40. Both the inlet tube 36 and the outlet tube 39 are sized to be sealingly engaged by the tubing set 16. which permits liquid to flow from the chamber.

The first housing member 32 has an annular shoulder 41 projecting from the floor of its recess at the circumference of it recess. The annular shoulder 41 and the annular rim 42 of the second housing member 34, when the second housing member 34 is fitted in the recess of the first housing member 32, form an annular clamp.

Figure 2A:
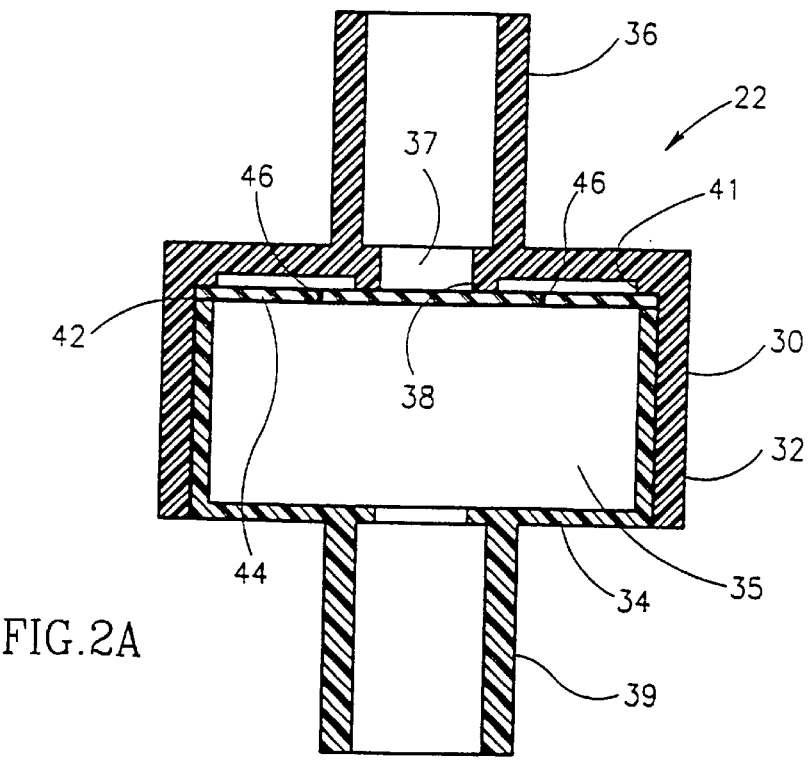
FIG. 2A is a longitudinal cross-sectional view of a valve for use in the system of FIG. 1 in a rest state.
Figure 2B:
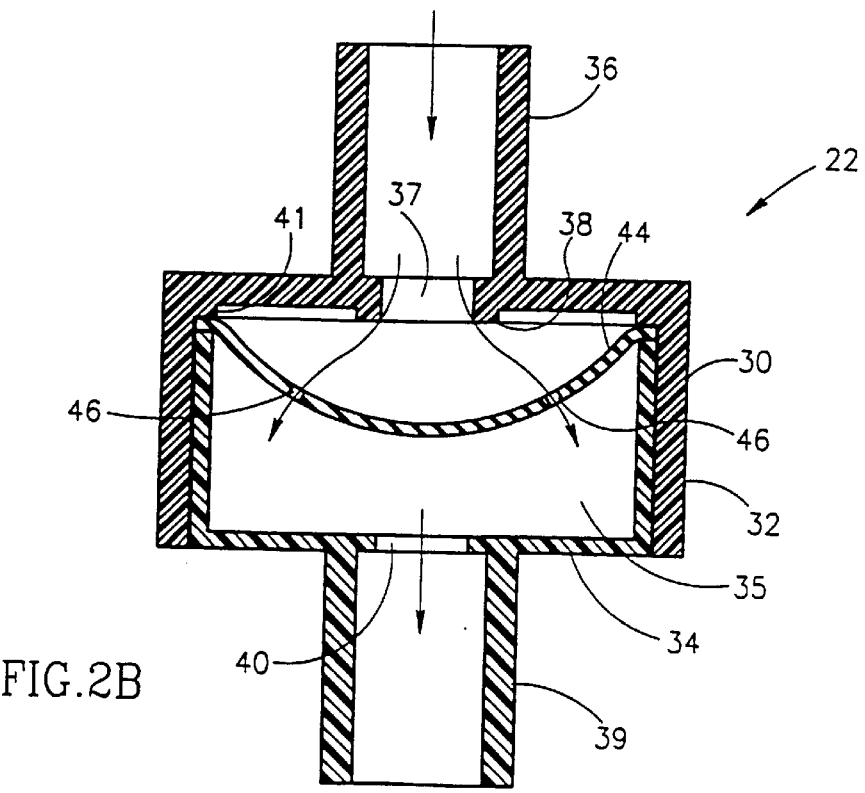
FIG. 2B is a longitudinal cross-sectional view of the valve of FIG. 2A in an operational state.

A resilient membrane 44 is clamped between the annular shoulder 41 and the annular rim 42 in the annular clamp. In the rest state of the valve 22 shown in FIG. 2A, the membrane rests on the annular rim 38 projecting from the first housing member 32. The membrane 44 is made of a resilient flexible material, typically sterilizable material such as silicon, rubber or any other suitable material. The membrane 44 has a plurality of slits 46 (two shown in this crosssectional view) which, in the rest state shown in FIG. 2A, are closed and do not permit flow of liquid through it.

When liquid is propelled through the inlet tube 36, the membrane 44 is stretched and deflected as shown in FIG. 21. Once a selected threshold pressure differential is reached and the membrane 44 is sufficiently stretched, the slits 46 widen and open to allow flow of liquid from the inlet tube 36, through the chamber 35, to the outlet tube 39). The flow is represented by the arrows in FIG. 2B. Typically, the membrane 44 is designed so that slits 46 will open only when the pressure differential over the membrane exceeds about 20 kPa. This prevents undesired free flow of the liquid from the container 18, which in a clinical setting is typically placed on a stand of a height of about 2 meters.

For flow in the reserve direction, the membrane 44 cannot deflect sufficiently since it is held against the floor of the recess of the first housing member 32. Therefore the valve 22 also prevents lack flow of liquid.

In use, the control unit 15 causes the pump 14 to operate in a duty cycle which has an administration phase and a test phase. The test phase is entered at selected, intermittent intervals. Typically, test phase is entered immediately after the pump system 10 has been set up, prior to initiation of the first administration phase. Thereafter, the test phase is entered at selected intervals, which may be randomly selected, between consecutive administration phases. Thus, the pump 14 may operate in a duty cycle of a first test phase, followed by an administration phase and then repeatedly through test phases and administration phases. In general, the test phases are of much shorter duration than the administration phases.

During the test phase, the integrity of the flow set 12 is checked. Also, correct assembly of the system 10 and the presence of the correct components of the flow set 12, and particularly the valve 22, arc checked. Further, the existence of air pockets or bubbles in the tubing set 16 may be detected.

Figure 3A:
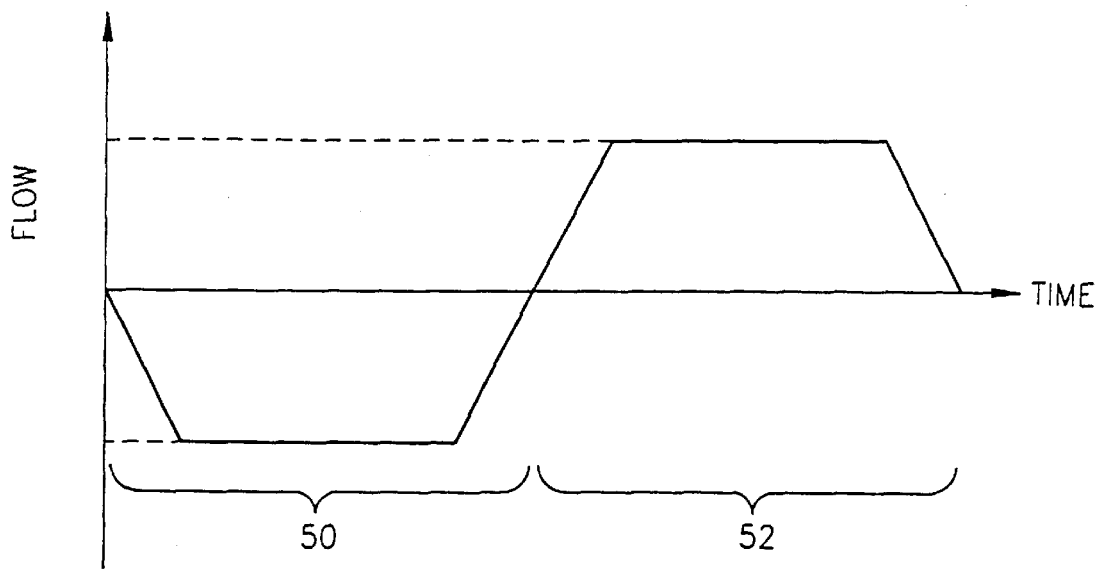
FIG. 3A is a graph of the flow of liquid versus time during a test phase of the pump system.
Figure 3B:
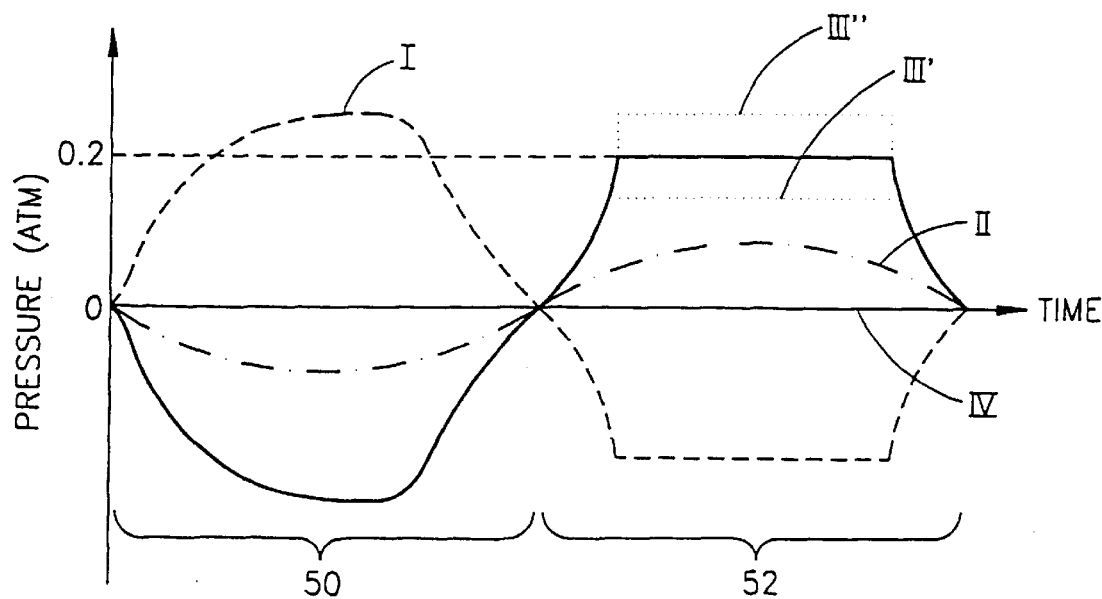
FIG. 3B is a graph of the pressure build-up versus time during a test phase of the pump system.

A test phase sequence is shown graphically in FIG. 3. As illustrated in FIG. 3A, during a first step 50 of the test phase, the pump 14 propels a small amount of liquid, for example about 0.5 ml, in a reverse direction, and then, in a second step 52, propels another small amount of liquid, for example about 0.4 ml, in a forward direction. The pressure change, relative to atmospheric, in the downstream portion of the flow set 12 (that is between the pump 14 and the valve 22) is shown in FIG. 3B.

If the pump system 10 has no faults, the pressure change is given by the solid line in FIG. 3B. In the first step 50, the pressure drops below atmospheric. In the second step 52, the pressure increases above atmospheric. The pressure is expected, in the second step 52, to increase to the cracking (threshold) pressure of the valve 22. As mentioned above, this is typically about 20 kPa. This pressure is maintained while the pump 14 is operating. When the pump 14 is then stopped, the pressure slowly declines to the zero level. This pressure curve, the no-fault curve, forms a standard which is stored in the microprocessor.

There may be several operative faults in the pump system 10. One possible fault is reverse assembly of the valve 22 in the flow set 12. Another possible fault is the reverse engagement of the pump 14 with the flow set 12 (in which case the pump 14 in a "forward" operational state in fact propels liquid in a reverse direction). Both of these faults will result in a pressure curve which is essentially a mirror image of the standard pressure curve. This faulty pressure curve is shown in FIG. 3B by the dashed line marked I. Another possible fault is leakage in the flow set 12 or the existence of air pockets or air bubbles (e.g. as foam) in the flow set 12. In this case, the pressure changes will be more moderate pressure than that of the standard curve; this is shown in FIG. 3B by the dashed-dotted lines marked II. A further possible fault state occurs when a valve 22 with an incorrect cracking pressure is used. In this case, the pressure curve during the first step 50 will be essentially the same as the standard curve. However, during the second step 52, the pressure will reach higher or lower maximum value than the standard curve; this is represented in FIG. 3B by dotted lines III' and III", respectively. Yet another possible fault is where the valve 22 is omitted entirely. In this case there will be substantially no pressure change and the pressure curve will essentially follow the abscissa (marked IV in FIG. 3B).

It will be appreciated that, in the test phase, the pump 14 need not first propel liquid in the reverse direction and then in the forward direction. In particular, this sequence may be reversed such that, during the test phase, the pump 14 first propels liquid in the forward direction and then in the reverse direction. This is merely a matter of appropriately setting the control unit 15. However, in this case, the standard pressure curve should be appropriate for an inverted test sequence.

During the test phase, the pressure curve which is determined is compared to the standard pressure curve stored in the memory in the control unit 15. In the event that the determined pressure curve deviates from the standard curve, the microprocessor indicates the presence of an error. It will be appreciated that the microprocessor may permit small deviations from the standard curve prior to indicating the presence of an error.

Upon the microprocessor indicating the presence of an error, the control unit 15 may, depending upon the error detected, initiate an alarm signal and prevent the pump 14 from entering into an administration phase. This may not be necessary if the error is the existence of air bubbles or air pockets. In this case, the control unit may halt the pump 14 for a short period of time, typically about 30 seconds, to allow possible air pockets to rise up in the tubing set 16 towards the container 18. Then the control unit 15 causes the pump 15 to enter into another test phase. If this fault is not detected again, the pump 14 will then be induced to enter into an administration state.

It will be appreciated that numerous modifications may be made to the preferred embodiments without departing from the scope of the invention as set out in the claims. For example, it is not essential for a drip chamber 21 to be connected in the flow set 12. Similarly, it is not essential that the flow set 12 use a one way valve 22 as described above. Other valve types and arrangements may be used; for example a combination of a one way valve and a valve which opens upon a threshold pressure being reached.

I claim:

1. A pump system for administering a liquid from a container to a patient, the system comprising:
    a flow set comprising:
        a) a tubing set having an upstream end and a downstream end, the upstream end being connectable to the container for delivery of liquid to the patient, and
        b) a one-way valve system coupled to the tubing set which permits liquid flow to the patient when a pressure differential over the valve exceeds a threshold pressure, and which prevents back flow;
    a pump coupled to the flow set upstream from the one-way valve, the pump including:
    a sensing means for sensing a parameter indicative of the pressure in the flow set between the pump and the one-way valve; and
    a controller having a computing and memory means for determining deviation of the parameter from a standard, the deviation being indicative of an error in the flow set including omission of or reverse assembly of the one-way valve system or use of a one-way valve system having an incorrect threshold pressure.

2. A pump system according to claim 1 in which the controller causes the pump, during operation of the pump, to enter into a test phase at selected intervals, the test phase comprising a first test sequence in which the pump propels a first amount of liquid in a first direction through the flow set, and a second test sequence in which the pump propels a second amount of liquid through the flow set in a second direction, opposite the first; the sensing means sensing the parameter during the first test sequence and the second test sequence.

3. A pump system according to claim 1 in which the tubing set contains tubing having a diameter and the sensing means measures changes in the diameter of the tubing for sensing the parameter indicative of the pressure.

4. A pump system according to claim 3 in which the sensing means is a tube diameter gauge.

5. A pump system according to claim 1 in which the valve system comprises a valve having a liquid flow path sealed by a resilient membrane, the membrane being deformable in a desired flow direction at or above a threshold pressure for opening perforations in the membrane to permit flow.

6. A pump system according to claim 5 in which the valve has a support preventing the membrane from deforming sufficiently in an opposite flow direction for preventing back flow.

7. A pump system for administering a liquid from a container to a patient, the system comprising:
    flow set comprising a tubing set having an upstream end and a downstream end, the downstream end being connectable to the container for delivery of liquid to the patient, and a one-way valve system coupled to the tubing set, the valve system including a valve having a liquid flow path sealed by a resilient membrane, the membrane being deformable in a desired flow direction at or above a threshold pressure for opening perforations in the membrane to permit liquid flow to the patient when a pressure differential over the valve exceeds a threshold pressure, and which prevents back flow;

a pump coupled to the flow set upstream from the one-way valve, the pump including:

a sensing means for sensing a parameter indicative of the pressure in the flow set between the pump and the one-way valve; and a controller having a computing and memory means for determining deviation of the parameter from a standard, the deviation being indicative of an error in the flow set including omission of or reverse of the one-way valve system or use of a one-way valve system having an incorrect threshold pressure.

8. A pump system according to claim 7 in which the controller causes the pump, during operation of the pump, to enter into a test phase at selected intervals, the test phase comprising a first test sequence in which the pump propels a first amount of liquid in a first direction through the flow set, and a second test sequence in which the pump propels a second amount of liquid through the flow set in a second direction, opposite the first; the sensing means sensing the parameter during the first test sequence and the second test sequence.

9. A pump system according to claim 7 in which the valve has a support preventing the membrane from deforming sufficiently in an opposite flow direction for preventing back flow.

10. A pump system according to claim 7 in which the tubing set contains tubing having a diameter the sensing means measures changes in the diameter of the tubing for sensing the parameter indicative of the pressure.

11. A pump system according to claim 10 in which the sensing means is a tube diameter gauge.

12. A method for administering a liquid from a container to patient using a pump system, the method comprising:

pumping liquid through a flow set from the container to the patient through a one-way valve system positioned downstream of the pump system, the one-way valve system permitting flow to the patient when a pressure differential over the valve system exceeds a threshold pressure, and which prevents back flow; and intermittently entering a test phase comprising:

pumping a first test amount of liquid in a first direction and then pumping a second test amount of liquid in an opposite direction, sampling a parameter indicative of pressure within the flow set between the pump system and the one-way valve system during pumping of the first test amount of liquid and during pumping of second test amount of liquid, and comparing the sampled parameters to a standard indicative of correct connection of a one-way valve system having a selected threshold pressure in the flow set and, upon determining a difference of selected magnitude between the sampled parameters and the standard, indicating the existence of an error in the pump system.

13. A method according to claim 12 in which the parameter indicative of pressure is sampled by determining changes in the diameter of tubing in the flow set.

14. A method according to claim 13 in which the pump enters a test phase prior to pumping liquid to the patient.

* * * * *

UNITED STATES PATENT AND TRADEMARK OFFICE
CERTIFICATE OF CORRECTION

PATENT NO. : 5,951,510
DATED      : September 14, 1999
INVENTOR(S) : Swi Barak

It is certified that error appears in the above-identified patent and that said Letters Patent is hereby corrected as shown below:

Title page, item [73] Assignee: should read --Nestec S.A., Vevey, Switzerland--.

Signed and Sealed this

Thirtieth Day of May, 2000

Attest:

Q. TODD DICKINSON

*Attesting Officer*   *Director of Patents and Trademarks*